United States Patent [19]
Korisch et al.

[11] Patent Number: 5,951,526
[45] Date of Patent: Sep. 14, 1999

[54] SYRINGE HOLDER WITH INTEGRAL DOSE DIVIDER

[76] Inventors: Marina Korisch, 91 Strawberry Hill Ave. #639, Stamford, Conn. 06902; Paul G. Alchas, 29 Ponds Cir., Wayne, N.J. 07470; Claude Imbert, 10 Chemin Concorde, 38700 La Tronche, France

[21] Appl. No.: 08/936,370

[22] Filed: Sep. 24, 1997

[51] Int. Cl.[6] .................................................. A61M 5/00
[52] U.S. Cl. ............................................ 604/208; 604/232
[58] Field of Search .................................. 604/187, 189, 604/207–210, 218, 227, 228, 232, 234–236, 238, 233, 246–249, 94; 222/343, 183, 326, 309, 386, 325; 128/840, 839, 203.18, 203.22; 424/434

[56] References Cited

U.S. PATENT DOCUMENTS

| | | | |
|---|---|---|---|
| 2,216,354 | 10/1940 | Pletcher | 222/309 |
| 2,720,880 | 10/1955 | Whitaker et al. | 604/232 |
| 2,792,157 | 5/1957 | Gilman | 222/309 |
| 2,875,761 | 3/1959 | Helmer et al. | 604/187 |
| 4,357,971 | 11/1982 | Friedman | 141/27 |
| 4,654,035 | 3/1987 | Ando | 604/210 |
| 4,962,868 | 10/1990 | Borchard | 604/210 |
| 5,009,645 | 4/1994 | Silver et al. | 604/207 |
| 5,279,586 | 1/1994 | Balkwill | 604/232 |
| 5,284,132 | 2/1994 | Geier | 604/94 |
| 5,514,107 | 5/1996 | Haber et al. | 604/197 |
| 5,601,077 | 2/1997 | Imbert | 604/237 |
| 5,624,400 | 4/1997 | Firth et al. | 604/110 |
| 5,662,098 | 9/1997 | Yoshida | 128/200.22 |
| 5,713,914 | 2/1998 | Lee | 604/54 |

*Primary Examiner*—Corrine McDermott
*Assistant Examiner*—Sharon Finkel

[57] ABSTRACT

An assembly for administering preset doses of medication is provided. The assembly includes a syringe holder and a pre-filled syringe which is mounted to the holder. The syringe includes a barrel for containing medication, a movable plunger including a piston within the barrel, and a blunt end having an opening through which the medication within the barrel can be expelled. The syringe holder includes a body portion and a movable stop which is engageable with the plunger of the syringe. The stop engages the plunger once it has been moved sufficiently to deliver a desired amount of medication from the barrel for example. The user then disengages the stop from the plunger, allowing the remaining medication to be administered. One application is to a nasal syringe, where approximately equal doses of medication are desired to be administered to each nostril of the patient.

9 Claims, 9 Drawing Sheets

SYRINGE HOLDER WITH INTEGRAL DOSE DIVIDER

BACKGROUND OF THE INVENTION

1. Field of the Invention

The field of the invention relates to devices for the administration of medication and, more particularly, to nasal syringes in which the travel of the plunger is controlled by a stop mechanism.

2. Brief Description of the Prior Art

A number of medications may be effectively administered through the nasal passages. Devices have accordingly been developed for this purpose, such as that described in U.S. Pat. No. 5,601,077. Nasal syringes of more conventional construction include a cylindrical barrel having a blunt tip portion for insertion into a nostril. A piston is positioned within the barrel. A plunger extends from the end of the barrel opposite to the blunt tip. The position of the piston within the barrel is controlled by the plunger. A flange may be provided on one end of the plunger to facilitate its use.

Nasal syringes are often supplied to users pre-filled with medication. Whether prefilled or not, it may be desirable to administer selected, and usually equal volumes of medication to each nostril. U.S. Pat. No. 4,962,868 discloses the use of a telescoping tube assembly which is designed for expelling the contents of a nasal syringe in two controlled doses.

While syringes often include graduations, it remains difficult for users to administer equal doses of medication to each nostril using conventional syringes. As such syringes are relatively inexpensive to manufacture and pre-fill, and are mass-produced, they have certain advantages over syringes which may be specifically designed for self-administration.

SUMMARY OF THE INVENTION

The invention is directed to an assembly which allows the use of a conventional, pre-filled syringe while providing control of the dose to be administered. The assembly is particularly applicable to nasal syringes where it is often desirable to dispense medication in two equal doses.

In accordance with the invention, an assembly is provided which includes a syringe holder, a syringe mounted into the syringe holder, and a stop which is movably coupled to the syringe holder. The syringe includes a barrel, a first end extending from the barrel and including an opening for dispensing fluid from the barrel, a piston slidably positioned within the barrel, and a plunger engageable with the piston. The stop is manually movable between a first position where it engages the plunger after the plunger has been moved a preselected axial distance, and a second position where the plunger and stop are not engageable. This allows the user to move the plunger a first selected distance corresponding to a first preselected dose, and then administer a second dose corresponding to the remaining contents of the syringe once the stop is displaced. The syringe can then be removed from the holder and discarded, or it can be discarded with the holder.

A syringe holder is also provided by the invention. The holder includes an elongate body which includes a cavity in which the barrel of a syringe can be positioned. A stop is pivotably secured to one end portion of the elongate body, and is movable between first and second rotational positions. When in the first position, the stop adjoins the longitudinal axis of the syringe holder. It accordingly is engageable with a flange of a plunger of the syringe extending from the holder when in this position.

The invention further provides an assembly for the nasal administration of fluids which limits the penetration of a syringe tip into a nostril. The assembly includes a syringe holder and a nasal syringe mounted into the syringe holder. The nasal syringe includes a blunt tip having a smaller diameter than the average nostril. It projects from a blunt end of the holder which is larger in diameter than that of an average nostril. The nasal syringe is maintained in the holder such that the blunt tip thereof cannot extend more than a selected distance beyond the blunt end of the holder.

DETAILED DESCRIPTION OF THE INVENTION

An assembly 10 including a syringe holder 12 and a syringe 14 is provided. The assembly allows the dose delivered by the syringe to be divided. It further limits the penetration of the tip of the syringe into the body of a user.

Figure 1:
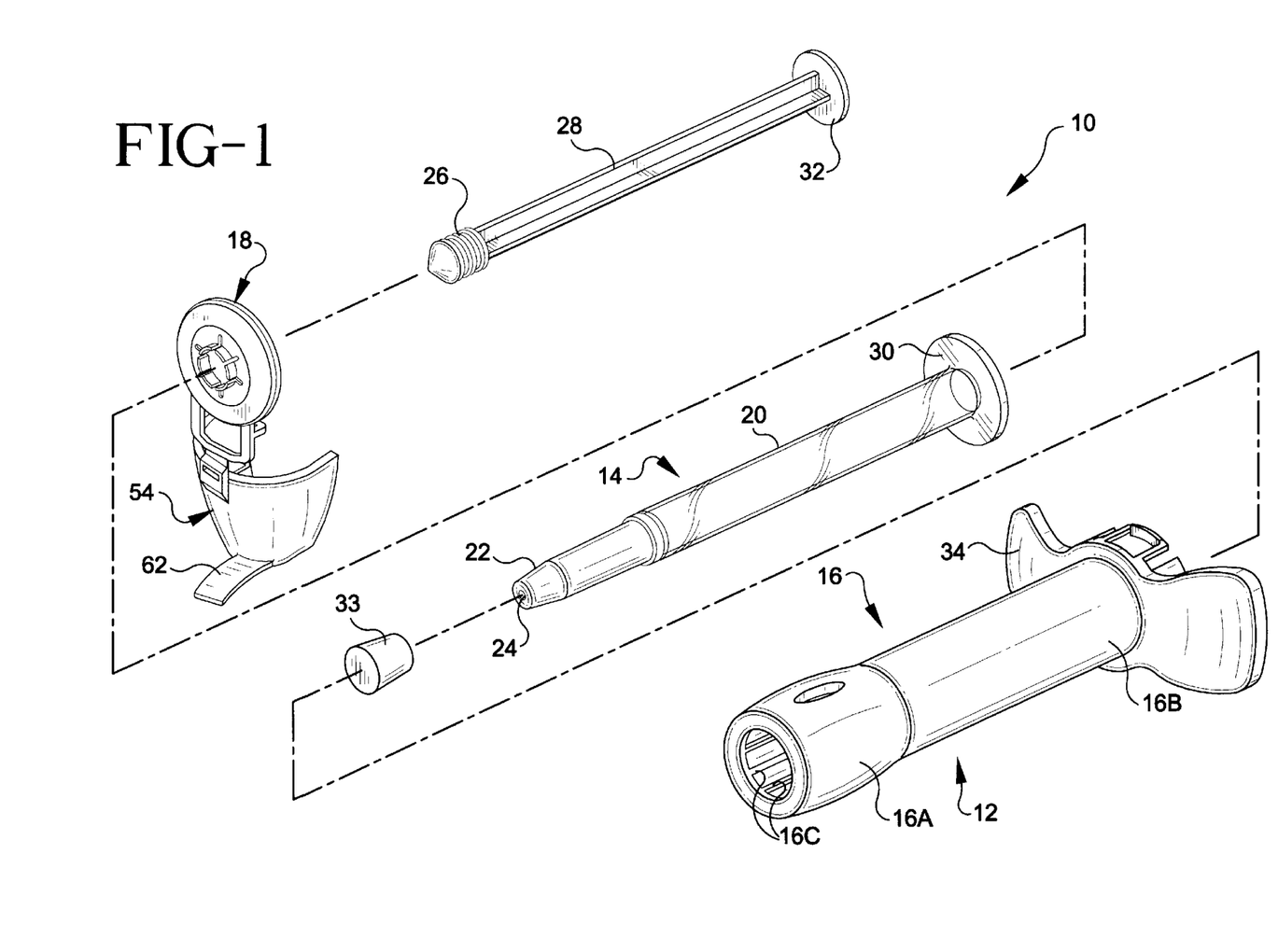
FIG. 1 is an exploded, perspective view of a syringe and holder assembly.
Figure 2:
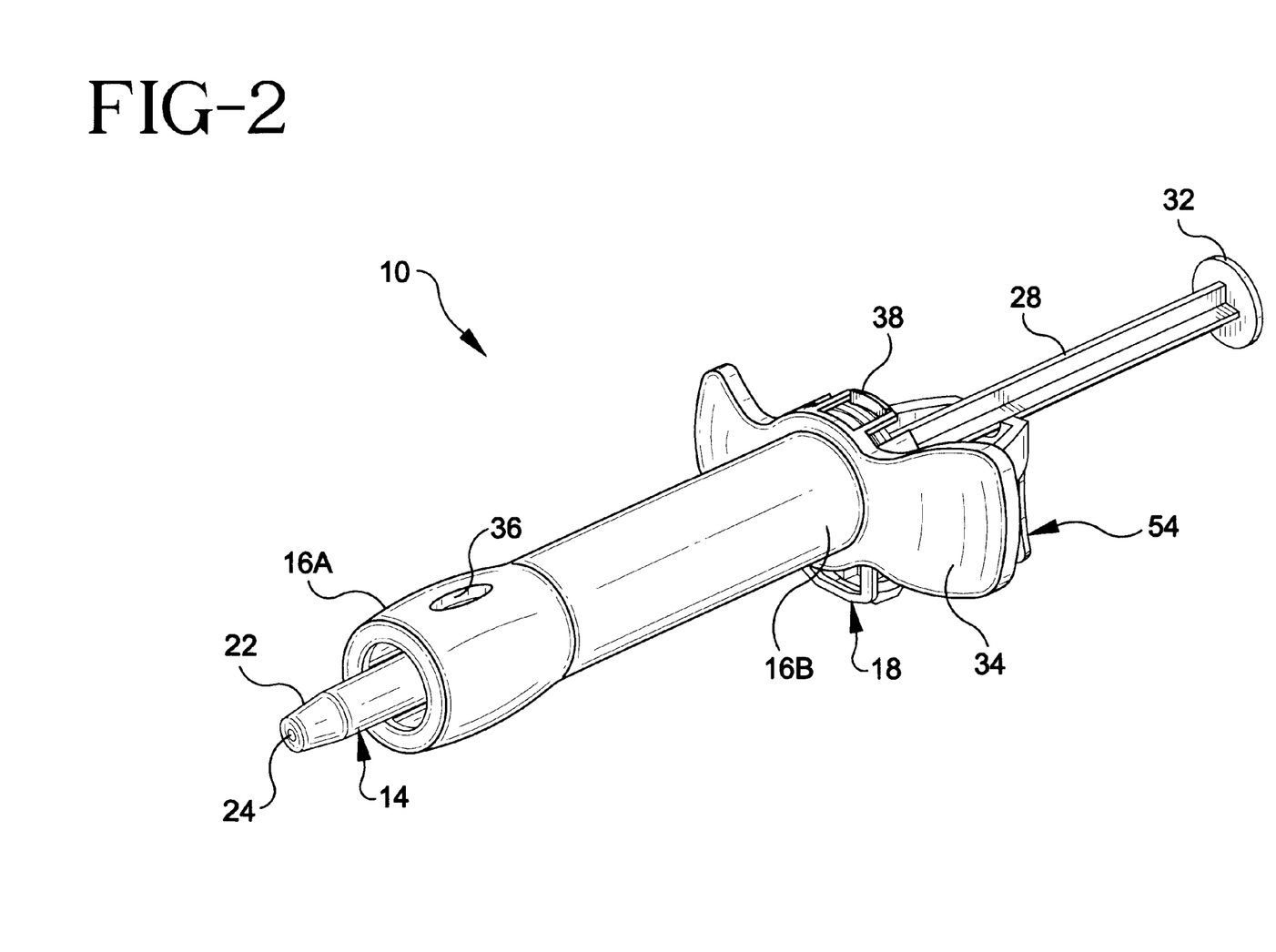
FIG. 2 is a top perspective view thereof.

Referring to FIGS. 1 and 2, the syringe holder is comprised of a tubular body 16 which includes a cavity 17 in which the syringe can be positioned and an end cap 18. The syringe is comprised of a cylindrical syringe barrel 20 having a blunt tip 22 including an orifice 24 through which fluid can be expelled, a piston 26 (shown in FIG. 3), and a plunger 28. The rear end of the barrel 20 of the syringe 14 includes a flange 30. A finger tab 32 is also integrally formed at one end of the plunger 28. As described below, the piston 26 and plunger 28 are preferably separate components, and can be engaged or connected with one another after the barrel has been mounted within the syringe holder, or if desired, they can be engaged or connected together prior to mounting the barrel in the syringe holder. The syringe is preferably pre-filled with medication prior to inserting it within the syringe holder. A sealing cap 33 may be fitted over the blunt tip 22 to prevent the loss of fluid through the orifice 24 prior to use of the assembly.

The tubular body 16 of the syringe holder 12 is ergonomically shaped to facilitate handling. It is preferably made from a plastic material such as polypropylene. The tubular body 16 includes a first, enlarged end portion 16A through which the blunt tip 22 of the syringe can extend, and a second end portion 16B including radially outwardly extending flanges 34. These flanges are larger than that provided on the barrel, and make the assembly more convenient for the user to operate than the syringe alone. The end face of the first end portion 16A is larger in diameter than the diameter of an average adult nostril, and is blunt. While the embodiment shown in the drawings has a first end portion 16A face which is rounded, it may alternatively be oval or any other shape desired, provided that the front end face is prevented from entry into the nostril.

One or more transparent windows 36 are provided in the tubular body 16 of the syringe holder. The windows may be in the form of openings in the tubular body, or transparent wall portions mounted to the tubular body. The windows allow the user to view the barrel 20 located within the holder syringe. The user can accordingly determine whether there is any fluid present in the syringe, and whether the fluid is suitable for administration. As some pharmaceutical products are frozen during storage, it may be important to determine whether the product within the syringe has thawed prior to administration.

The second end portion 16B of the holder syringe is designed to retain flange 30 of the barrel as well as a portion of the end cap 18. Second end portion 16B includes an end face defining an opening of sufficient size for receiving the barrel, but which is smaller in size than flange 30. The flange 30 accordingly bears against this end face when the syringe is mounted to the syringe holder. As shown in FIGS. 3–5 and 7, the inner surface of the tubular body 16 includes a plurality of axially extending ribs 16C. The ribs extend between the annular surface which forms the end face 16D of the first end portion 16A of the tubular body and the end face 16E of the second end portion 16B thereof. Flange 30 of the barrel thus bears against the ends of the ribs 16C, which may be considered part of one end face 16E of the tubular body. The ribs thus help to form the end face for supporting flange 30 of the barrel. Additionally, ribs 16C can serve to strengthen the structure of the syringe holder, and aids in the injection molding characteristics of the holder syringe.

A plurality of projections extend axially from the rear end face of the syringe holder, defining a generally cylindrical extension of the tubular body 16. A pair of opposing projections 38, 40 include detents 42, 44 for retaining the end cap 18. The detents include angled end faces which allow the end cap to snap behind the detents. Shoulder portions defined by the inner surfaces of the detents lock the end cap in place. The remaining projections 45 prevent the radial displacement of the end cap and obscure the flange 30 of the syringe.

The end cap 18 includes a generally annular body 46 having a central opening 48 aligned with the longitudinal axes of the syringe holder and syringe. Central opening 48 preferably displays a diameter less than the outer diameter of piston 26 so as to prevent piston 26 from inadvertent withdrawal from cylindrical barrel 20. A plurality of deflectable tabs 50 extend axially towards the syringe, and bear against the end face of the flange 30. The flange 30 is accordingly locked in position between the tabs and the end face of the second end portion 16B of the syringe holder. The end cap further includes an axially extending projection 52 which functions as a detent in a manner described below. Projection 52 extends from a radial projection 53 having an opening 53A which receives one of the projections 38, 40 extending from the tubular body.

Figure 4:
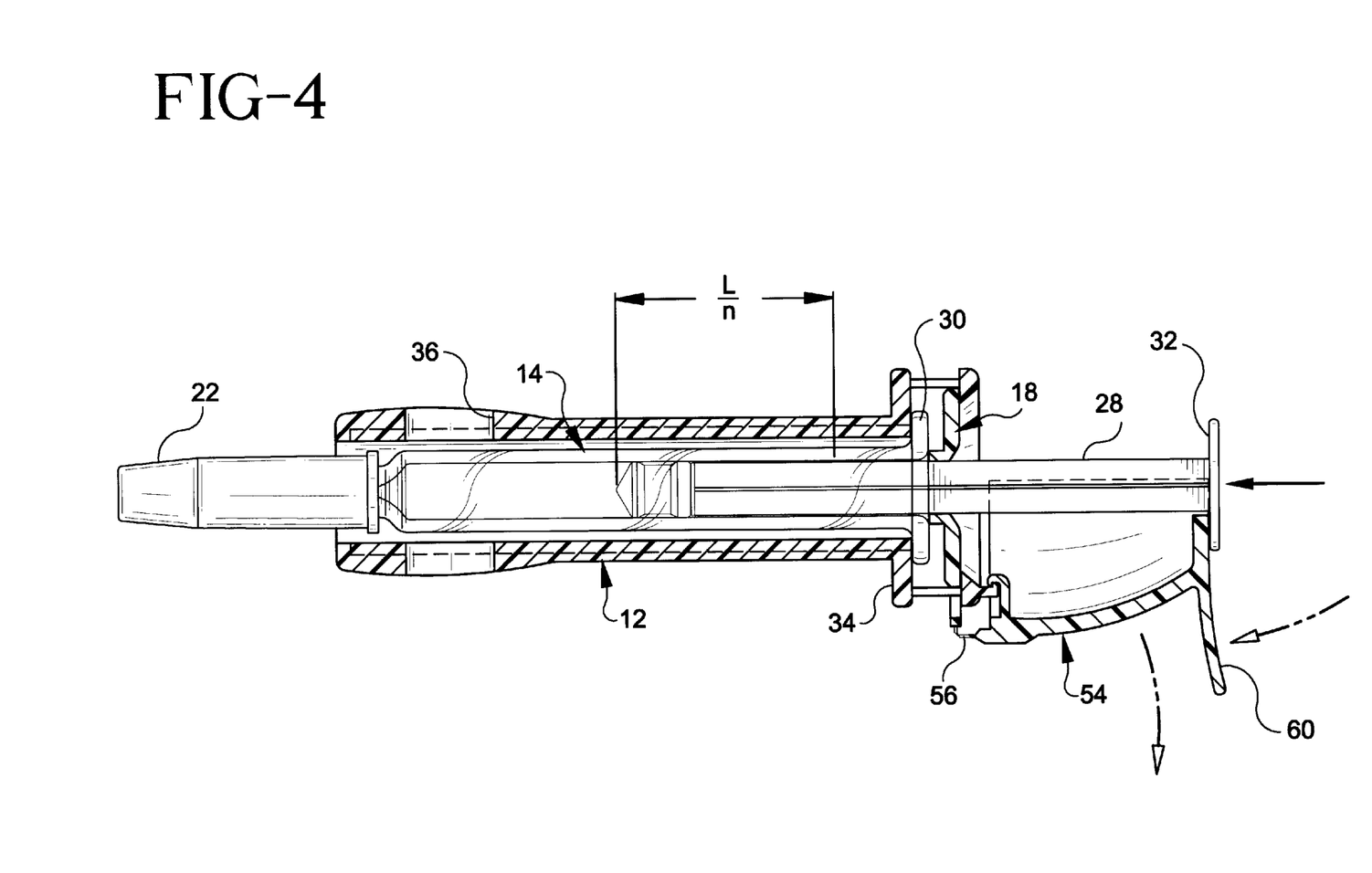
FIG. 4 is a partially sectional, elevation view thereof showing the plunger of the syringe in engagement with a stop.

A stop 54, which functions as a dose divider, is coupled to the end cap 18 by a hinge 56. Hinge 56 can be formed in any manner known to the skilled artisan, such as a pivot, for instance. Here, it is depicted as a so-called "living hinge" connecting end cap 18 and stop 54. Stop 54 includes a hook-like projection 58 near one end and end cap 18 includes the projection 52, which likewise can assume a hooked structure. Stop 54 is engageable with the projection 52 of the end cap as the stop is pivoted towards the end cap in the locked position. The opposite end of stop 54 includes a stop surface 60 which is engageable with the finger tab 32 of the plunger 28 as shown in FIG. 4. A finger tab 62 is also provided at this end of the syringe holder for manually rotating the stop about the hinge 56. In one configuration, body portion 64 of the stop can be formed as a partial frustoconical.

Figure 3:
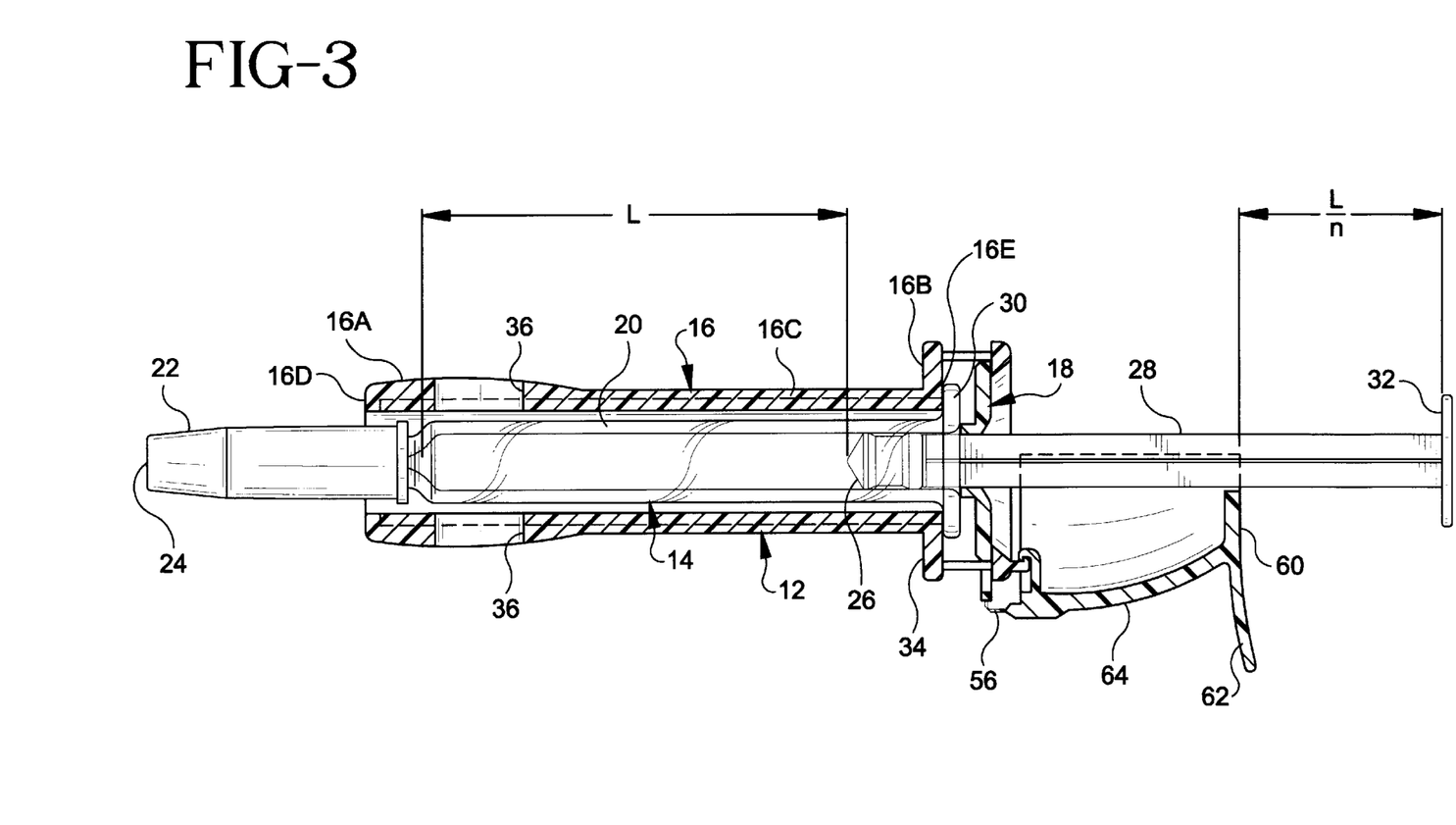
FIG. 3 is a partially sectional, elevation view thereof showing the plunger of the syringe in a first position.

Syringe 14 is preferably filled and stoppered prior to its insertion into the tubular body 16 of the syringe holder 12. The flange 30 is configured such that it engages end face 16E of the tubular body. Upon such engagement, the tip 22 of the syringe extends a selected distance beyond the first end portion 16A of the tubular body. This feature limits the penetration of the tip into a nostril of the patient when the assembly is employed. The end cap 18 is snapped into place behind the detents 42, 44, thereby locking syringe 14 in the holder syringe 12. The deflectable tabs 50 bear against the flange 30 of the syringe, as shown in FIG. 3. The engagement of one of projections 38 or 40 in opening 53A of the end cap serves to prevent inadvertent rotation of the end cap with respect to syringe holder 12, thereby ensuring uniform orientation of the end cap during administration of the drug.

Finally, plunger 28 is moved through the central opening 48 in the end cap and into engagement with the piston 26. It will be understood that if it is desired to preassemble plunger 28 to syringe 14 before placement in syringe holder 12, then an appropriate opening (not shown) can be incorporated in end cap 18 to allow lateral displacement vis-à-vis plunger 28. The assembly is ready for use upon engaging the projections 52 and 58, locking the stop 54 into the position shown in FIG. 3, whereby the stop surface 60 is relatively close to the longitudinal axes of the syringe holder and syringe and in position to engage the finger tab 32.

In operation, the assembly 10 as shown in FIG. 3 is grasped by the user and the blunt tip 22 inserted into a nostril. The plunger 28 is then pushed into the syringe, causing the displacement of the piston 26 and expulsion of a predetermined contents of the barrel through the orifice 24, depending upon the distance that finger tab 32 of the plunger 28 of the syringe travels until its progress is arrested by stop 60, as shown in FIG. 4. For simplicity, the total distance that piston 26 may be displaced into syringe 14 is depicted by the legend "L" on FIG. 3, with that distance "L" also correlated to a total quantity of drug held by the barrel of the syringe. Similarly, the displacement of piston 26 a distance L/n, as seen in FIGS. 3 and 4, correlates to a first desired quantity of the drug to be administered from the syringe during a first motion of plunger 28. For instance, for an application to a nasal syringe, it is typically desirable to ensure equal administration of drug into each of the nostrils, meaning that it would be desired to expel only half of the contents of the syringe at such time as finger tab 32 is arrested by stop surface 60 (thus, adverting to FIGS. 3 and 4, L/n would correlate to L/2).

Figure 5:
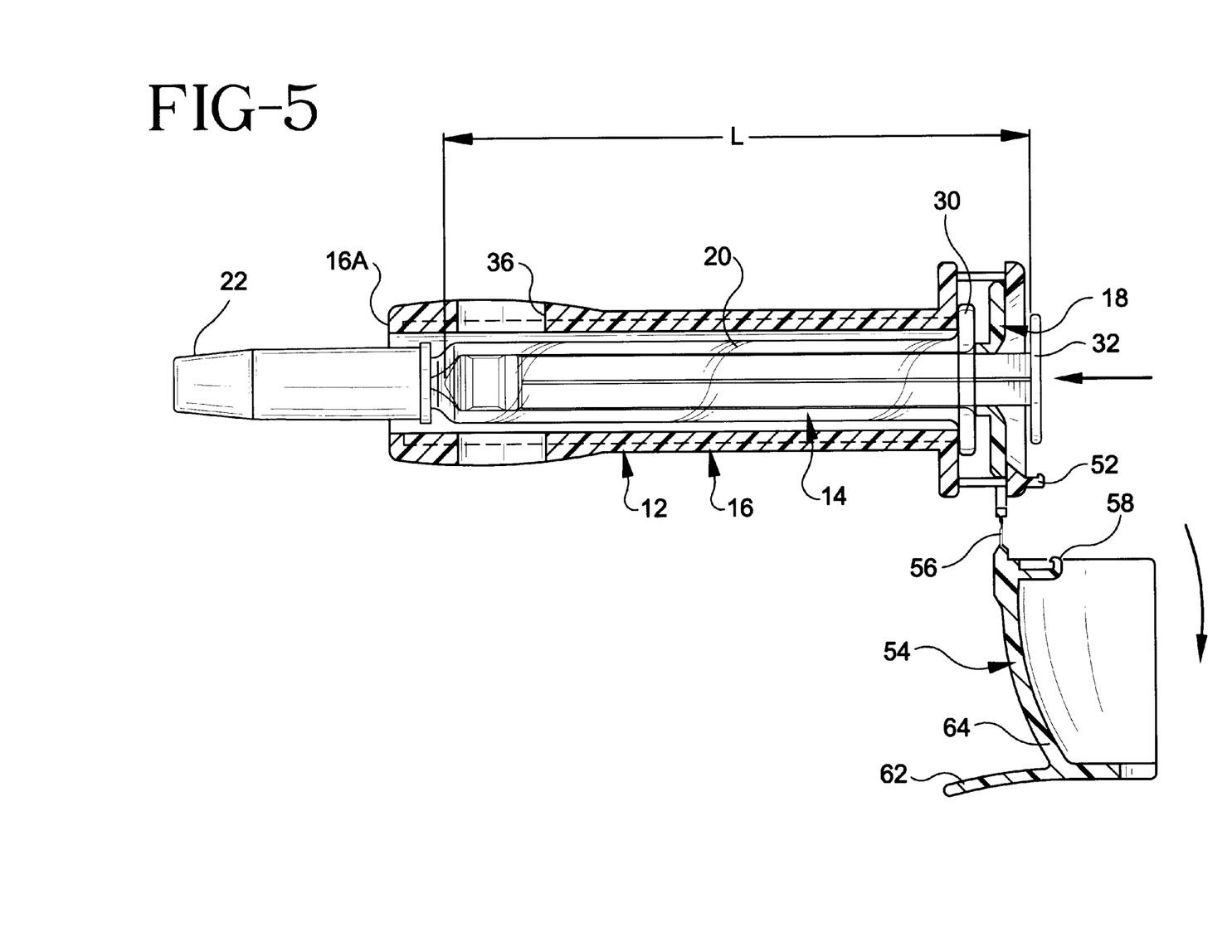
FIG. 5 is a partially sectional, elevation view thereof showing the plunger of the syringe in a fully inserted position and the stop in a rotationally displaced position.
Figure 6:
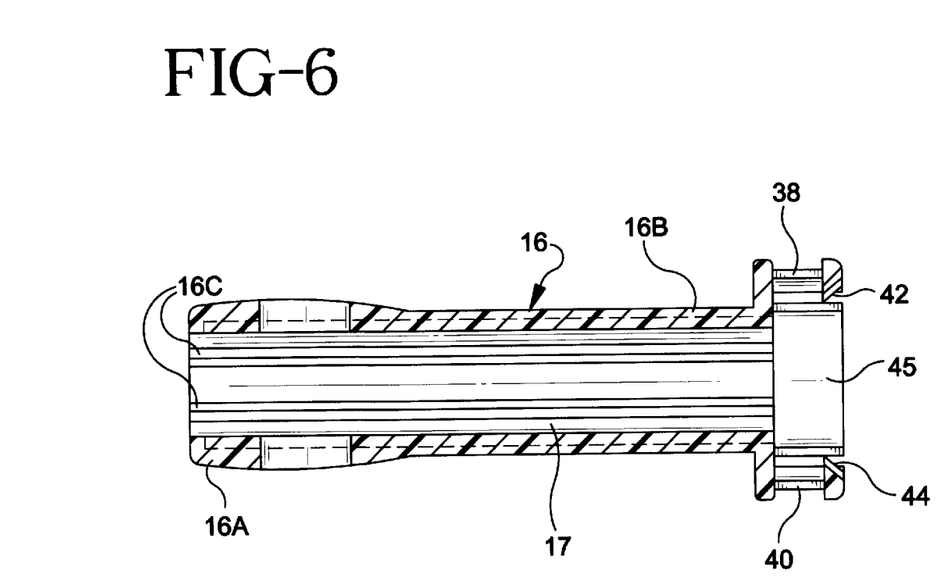
FIG. 6 is a sectional view showing the tubular body of a syringe holder.
Figure 7:
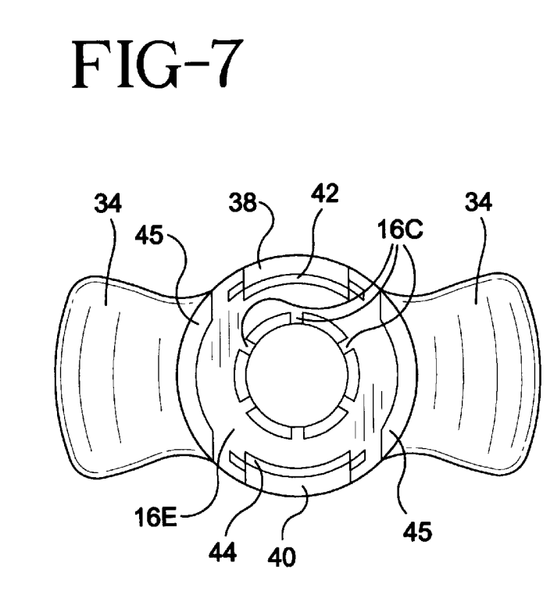
FIG. 7 is an end view thereof.
Figure 8:
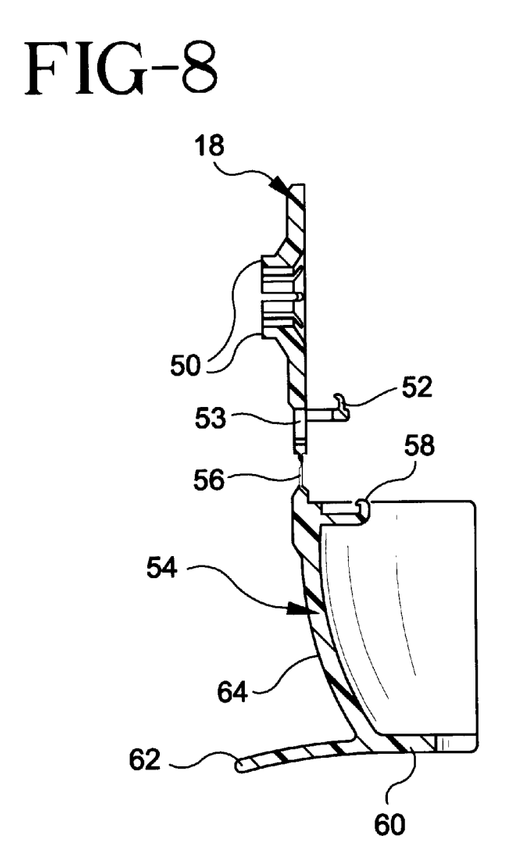
FIG. 8 is a sectional view of an end cap of the syringe holder and a stop pivotally secured stop thereto.
Figure 9:
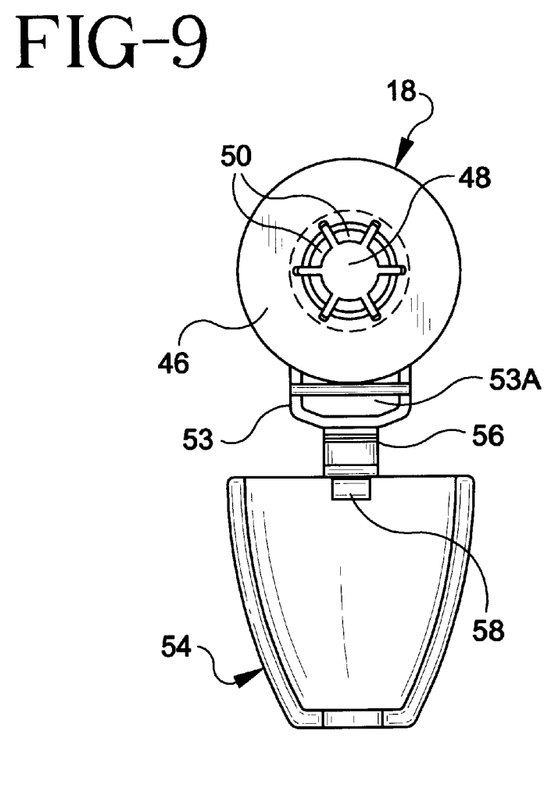
FIG. 9 is an end view thereof.

After a first administration of the drug, then, using the finger tab 62 of stop surface 60, the stop is disengaged from the detent 52 and rotated about the living hinge 56. Once the stop surface 60 has been displaced sufficiently such that it is no longer engageable with the finger tab 32 of the plunger, the plunger is again advanced to expel the remaining contents of the syringe into the other nostril. FIG. 5 shows the assembly 10 once the contents have been expelled. Once so used, the entire assembly is typically discarded.

Figure 10:
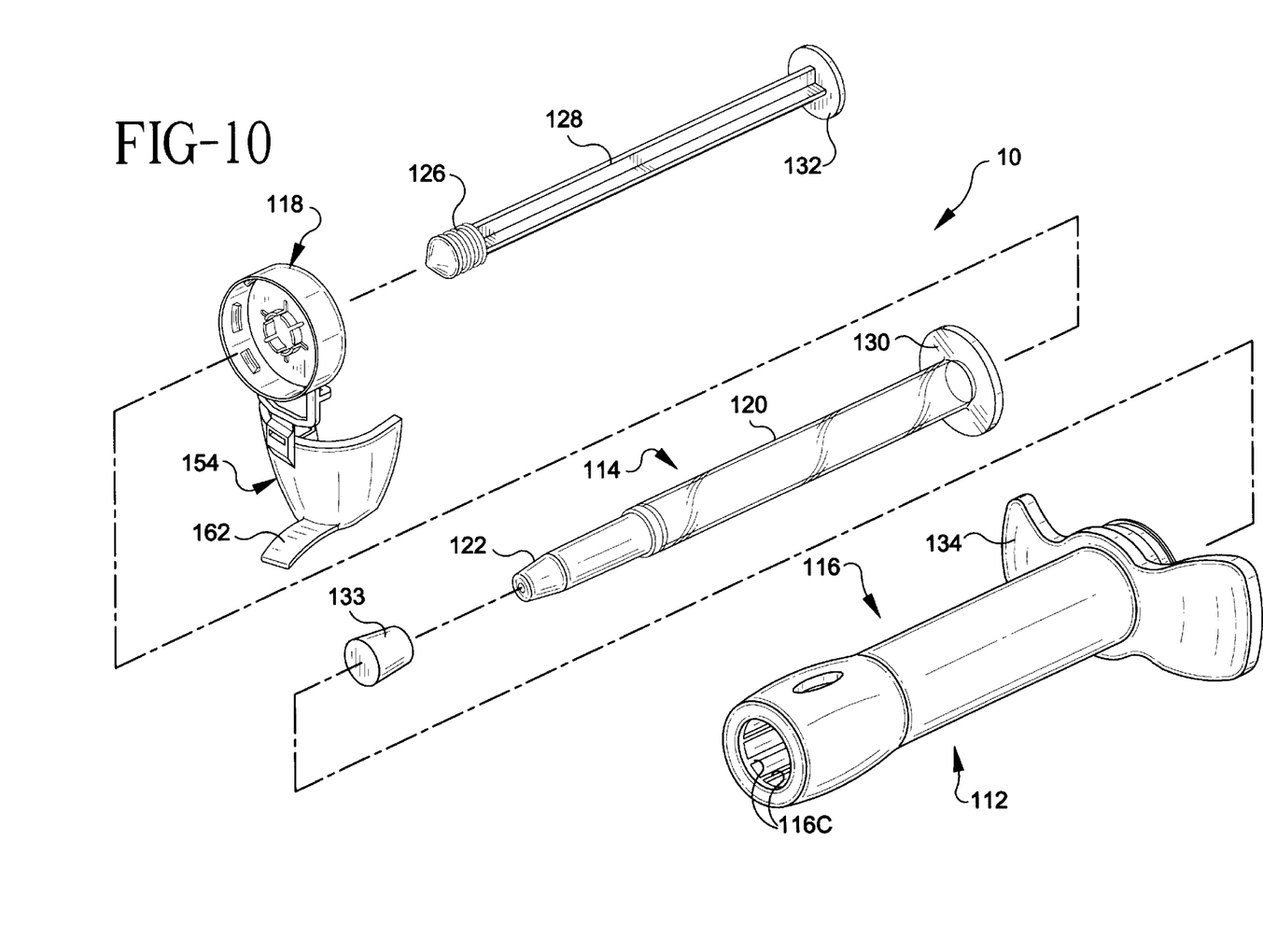
FIG. 10 is an exploded view of an alternate way to connect the end cap to the syringe holder.
Figure 11:
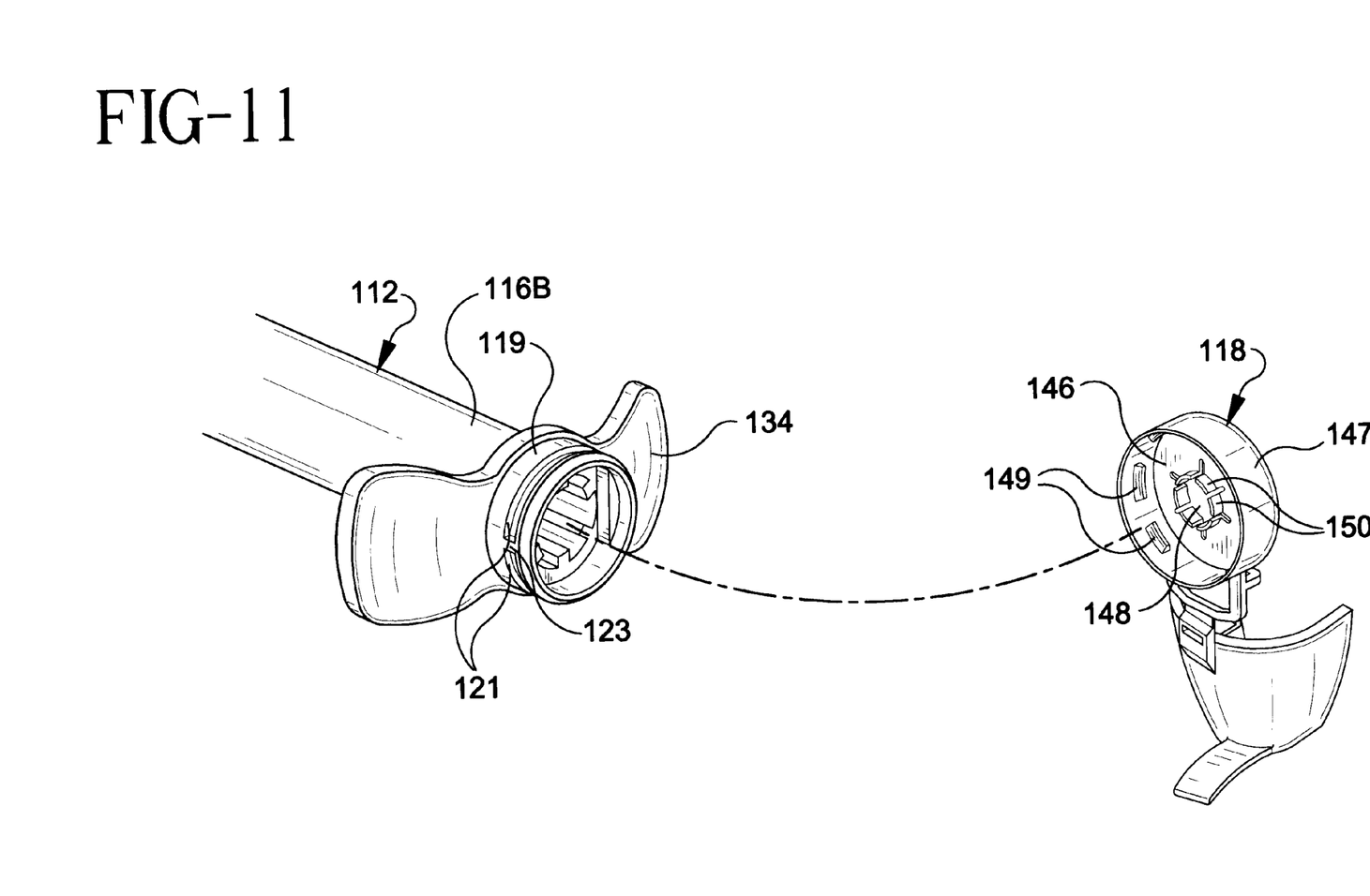
FIG. 11 is a partial view depicting attachment of the end cap to the holder of FIG. 10.

FIGS. 10 and 11 illustrate an alternate way to affix the end cap to the syringe holder. Where appropriate, identical elements to the embodiment shown in FIGS. 1–9 have been correspondingly numbered, save for the addition of the numeral "1". Here, as before, end cap 118 includes a generally annular body 146 that includes a cylindrical wall 147. As before, end cap 118 includes a central opening 148 and a plurality of deflectable tabs 150. Second end portion 116B of syringe holder 112 is structured to include a cylindrical wall 119. Cylindrical walls 119, 147 of the syringe holder and end cap are configured for locking/mating contact with one another. Here, groove 121 is formed in cylindrical wall 119 that is complementary to a plurality of tongues 149 provided on cylindrical wall 147. Tongues 149 are engaged by groove 121. Of course, the positioning of the tongues and grooves can be reversed. Groove 121 can be interrupted, such as by providing stops 123, to prevent end cap 118 from inadvertent rotation about syringe holder 112.

The assembly 10 provides a number of advantageous features. It allows the user to easily divide the dose to be delivered by the syringe through manipulation of an integral stop. When used with a nasal syringe, the enlarged end of the syringe holder limits the penetration of the syringe tip into the nostril. The configuration of the holder together with its enlarged flanges facilitate its handling and use. Manipulation of the stop is possible with one finger, while the assembly requires the use of only one hand.

It will be appreciated that modifications can be made to the preferred embodiment disclosed herein without departing from the spirit of the invention. The scope of the invention should accordingly be determined by the appended claims.

What is claimed is:

1. An assembly for the nasal administration of fluids, comprising:
    a syringe holder including an elongate body portion having a blunt end portion and a second end portion, said body portion defining a cavity between said first and second end portions, and
    a pre-filled nasal syringe mounted to said syringe holder, said nasal syringe including a barrel positioned within said cavity of said syringe holder, a first end having a blunt tip and an opening in said blunt tip for dispensing fluid from said barrel, a second open end, a piston within said barrel, and a plunger positioned partially within said barrel and extending through said second open end of said nasal syringe, said plunger having an end extending beyond said second end portion of said syringe,
    said blunt end portion of said syringe holder having a larger diameter than the average diameter of a nostril of an adult patient which limits the penetration of the blunt tip of the nasal syringe into a nostril of an adult patient, said blunt tip of said nasal syringe extending beyond said blunt end portion of said syringe holder and being restricted by said syringe holder from extending beyond said blunt end portion by a selected distance, said blunt tip of said nasal syringe having a diameter which is less than the average diameter of a nostril of the adult patient; and
    a stop pivotably mounted to said syringe holder and movable between a first position wherein said stop is engageable with said plunger and a second position wherein said stop is not engageable with said plunger, and means for releasably retaining said stop in said first position.

2. An assembly as described in claim 1 wherein said second end portion of said syringe holder includes a radially outwardly extending flange.

3. An assembly as described in claim 1 wherein said stop includes a first end pivotally secured to said syringe holder and a second end including a finger tab.

4. An assembly as described in claim 1 including a cap secured to said second end portion of said elongate body portion, said nasal syringe including a flange positioned between said cap and said second end portion.

5. An assembly as described in claim 1 wherein said plunger includes a flange, said stop being engageable with said flange when in said first position.

6. An assembly as described in claim 5 wherein said stop being manually movable between said first and second positions wherein said plunger is engageable with said stop upon moving a preselected axial distance and a second position wherein said plunger and stop are not engageable.

7. An assembly as described in claim 6 wherein said syringe holder includes an open end through which said plunger extends and a radially outwardly extending flange adjoining said open end.

8. An assembly as described in claim 6 wherein said preselected axial distance corresponds to about a dosage of medicament held in said barrel desired to be administered in a first motion of said piston.

9. An assembly as described in claim 8, wherein said preselected axial distance corresponds to about half the distance that said piston is capable of moving within said barrel to administer about one-half of the dose contained by said barrel.

\* \* \* \* \*